United States Patent
Faustman et al.

(10) Patent No.: US 6,414,218 B1
(45) Date of Patent: Jul. 2, 2002

(54) MOUSE MODEL FOR RHEUMATOID ARTHRITIS

(75) Inventors: Denise L. Faustman, Weston; Takuma Hayashi, Malden, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/483,897

(22) Filed: Jan. 18, 2000

(51) Int. Cl.$^7$ .................. A01K 67/00; A01K 67/033; G01N 33/00; C12N 15/00
(52) U.S. Cl. ......................... 800/9; 800/3; 800/22
(58) Field of Search ................... 800/3, 22, 9

(56) References Cited

U.S. PATENT DOCUMENTS 5,675,060 A * 10/1997 Benoist et al. ............... 800/2
5,718,883 A * 2/1998 Harlan et al. ................ 424/9.2

OTHER PUBLICATIONS

Gurg, T. Systems for idendifying new drugs are often faulty. Science. vol. 278. pp. 1041–1042. 1997.*
Crystal, R. G. Transfer of genes to humans: early lessons and obstacles to success. Science. vol 270. pp. 404–410. 1995.*
Hang et al. A spontaneous rheumatoid arthritis–like disease in MRL/l mice. J. Exp. Med. vol. 155. pp. 1690–1701. 1982.*
Feldmann, et al. Rheumatoid arthritis. Cell. vol. 85. pp. 307–310. 1996.*
Kouskoff et al. Organ specific disease provoked by systemic autoimmunity. Cell. vol. 87. pp. 811–822. 1996, 1997.*
De Graaf et al., in *The Epidemiology of Chronic Rheumatism*, Dellgren and Ball, eds. (Blackwell, Oxford, 1963), pp. 446–456.
Gabriel et al., *J. Rheumatol.*, 26:1269–1274 (1999).
Hang et al., *J. Exp. Med.* 155: 1690–1701 (1982).
Hirano et al., *Eur. J. Immunol.*, 18:1797–1801 (1988).
Iijima et al., *J. Rheumatol.*, 26:755–756 (1999); James, *Clin Exp. Rheumatol.*, 17:392–393 (1999).
Iwakura et al., *Science* 253: 1026–1028 (1991).
James, *Clin. Exp. Rheumatol.*, 17:392–393 (1999).
Makino et al., *Jikken Dobutsu Exp. Animals*, 29:1–13 (1980).
Meenam et al., *Arthritis Rheum.*, 24:544–550 (1981).
Ostensen, *Ann. N.Y. Acad. Sci.*, 876:131–143 (1999).
Pozzilli et al., *Immunol., Today*, 14:193–196 (1993).
Uhlig et al., *Ann Rheum Dis* 58:415–422 (1999).
Wilder et al., *Ann. N.Y. Acad. Sci.*, 876:14–31 (1999).

* cited by examiner

Primary Examiner—Deborah J. R. Clark
Assistant Examiner—Peter Paras, Jr.
(74) Attorney, Agent, or Firm—Leon R. Yankwich

(57) ABSTRACT

Nonobese Diabetic Mice (NOD mice) that do not develop diabetes may be bred to produce $F_1$ offspring that develop a condition that closely mimics rheumatoid arthritis (RA) in humans. The RA-like disease in the $F_1$ mice, designated NOD-RA mice, is similar to human RA in clinical, radiological, histological and serological characteristics. The parents ($F_0$) and their progeny ($F_1$) are not diabetic and never develop hyperglycemia, and the parental mice ($F_0$) do not themselves exhibit any symptoms of the RA-like condition that afflicts some of their progeny. The incidence, penetrance, gender domination, progression, and lifelong exacerbation of symptoms after pregnancy shown in the RA-like condition afflicting NOD-RA mice are all comparable to phenomena observed in the human disease. The NOD-RA mice provide a new spontaneous model of human RA that will be useful for studying rheumatoid arthritis and testing new drugs and reagents for treating or diagnosing the disease.

13 Claims, 7 Drawing Sheets

BALB/c

NOD-RA

MOUSE MODEL FOR RHEUMATOID ARTHRITIS

FIELD OF THE INVENTION

The present invention pertains to the field of medical research, particularly to the development of mammalian models of human rheumatoid arthritis.

BACKGROUND OF THE INVENTION

Rheumatoid arthritis (RA) is a common autoimmune disease characterized by joint swelling, deformation and, ultimately, destruction, culminating in severe physical disability. De Graaf et al., in *The Epidemiology of Chronic Rheumatism*, Dellgren and Ball, eds. (Blackwell, Oxford, 1963), pp. 446–56; Meenam et al., *Arthritis Rheum.*, 24:544–50 (1981); Gabriel et al., *J. Rheumatol.*, 26:1269–74 (1999); James, Clin. Exp. *Rheumatol.*, 17:392–93 (1999). RA is a progressive condition with well-recognized symptoms including symmetrical peripheral joint swelling and synovial inflammation while sparing the axial skeleton; the presence of rheumatoid factor (RF) autoantibodies; increased concentrations of interleukin-6 (IL-6) in serum and synovial fluid; and pregnancy-induced disease remission followed by severe postpartum flares, that is, while women with RA commonly undergo remission during pregnancy, the disease returns and may be even more severe and show a new onset or more accelerated course after delivery. See, Turgen, in *Immunology and Serology in Laboratory Medicine*, $2^{nd}$ edition, Shanahan, ed. (Mosby Year Book, St. Louis, 1996), pp. 387–98; Hirano et al., Eur. *J. Immunol.*, 18:1797–1801 (1988); Wilder et al., *Ann. N.Y. Acad. Sci.*, 876:14–31 (1999); Iijima et al., *J. Rheumatol.*, 26:755–56 (1999); Ostensen, *Ann. N.Y. Acad. Sci.*, 876:131–43 (1999).

In medical research directed to understanding, diagnosing and treating RA, several animal models of the disease have been described, but no spontaneous animal model that closely mimics all the features of the human disease has been discovered. Thus, it would greatly advance discovery research in the field of RA research if a mammalian model faithfully exhibiting the same characteristic physical symptoms of RA could be obtained.

It has now been surprisingly discovered that a particular breed of mouse commonly used in diabetes research, i.e., the nonobese diabetic or "NOD" mouse, can be used to produce offspring that exhibit a physical symptomology closely matching the symptomology of RA in humans suffering from the disease.

SUMMARY OF THE INVENTION

Accordingly, the present invention provides NOD mice useful as models of human rheumatoid arthritis, e.g., that exhibit joint and limb swelling, symmetrical enlargement of peripheral joints with sparing of axial skeleton (e.g., hips, spine); common tendon deformities, such as spontaneous rupture of extensor tendons and Boutonniere deformity; characteristic histological features, such as synovitis, leukocyte invasion, pannus formation, cartilage destruction and bone degeneration; and characteristic serological changes, such as autoantibodies specific for the Fc region of immunoglobulin G (IgG) and increases in proinflammatory cytokines, especially IL-6, in synovial fluid and serum. The occurrence of such symptoms in the mice, furthermore, mimcs the human disease in the pattern of progression of the disease and in disease penetration across a population. Moreover, the development of the disease in the mice shows the same disparate penetrance according to gender and the same pregnancy-correlated remission and postpartum exacerbation in females as observed in human RA sufferers.

The present invention also provides a method for preparing mouse models of human rheumatoid arthritis.

DETAILED DESCRIPTION OF THE INVENTION

Figure 1A:
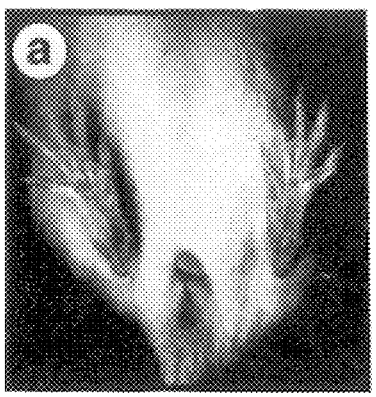
FIG. 1 (comprised of FIGS. 1*a* through 1*h*) illustrates the gross morphology of the hind feet of RA model NOD mice compared with non-RA BALB/c mice.
Figure 1B:
Figure 1C:
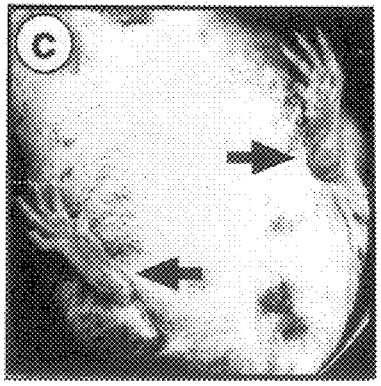
Figure 1D:
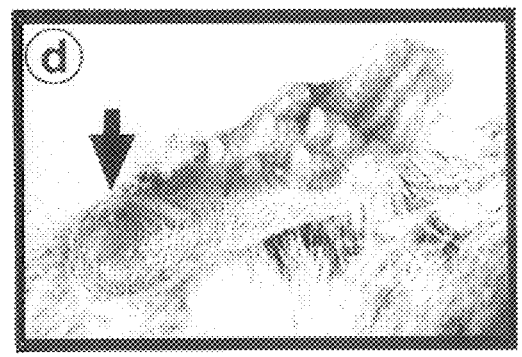

The present invention relates to a method for preparing mice that exhibit the physical characteristics (e.g., one or more symptoms) of human patients suffering from rheumatoid arthritis (RA) and thus provides a murine model of human rheumatoid arthritis. The mice prepared in accordance with the teachings herein are useful in studying the manifestation, penetration and progression of rheumatoid arthritis in humans, and the mice are also useful for testing new methods and products for the diagnosis and/or treatment of rheumatoid arthritis. The mouse model will be particularly useful for screening new drug candidates for effectiveness against RA.

The invention is based on the discovery that progeny (e.g., the first filial generation, or $F_1$) of nondiabetic (i.e., euglycemic) nonobese diabetic mice ("nondiabetic NOD mice"), develop the classical symptomology of rheumatoid arthritis by 20–28 weeks (or by 12–16 weeks after pregnancy). Moreover, the manifestation of the disease in the $F_1$ mice was confirmed by clinical (e.g., radiological, histological and serological) data that closely mimicked similar measurements in human RA patients.

Nonobese diabetic mice (NOD mice) are well known animal subjects for the -study of diabetes and other autoimmune diseases that affect humans. The mice are available commercially from several sources, e.g., Jackson Laboratory (Bar Harbor, Maine). NOD mice were first identified as developing spontaneous autoimmune diabetes in 1980 on the basis of cataract development that is a secondary characteristic of diabetes in humans. Makino et al., *Jikken Dobutsu Exp. Animals*, 29:1–13 (1980). Ninety percent (90%) of female NOD mice will develop autoimmune diabetes by 20 to 30 weeks of age; and about 20% to 40% of male NOD mice develop autoimmune diabetes. The diabetes that develops in NOD mice is lethal, and without insulin treatment NOD mice that become diabetic die within about 48 hours, with blood glucose concentrations of approximately 600 mg/deciliter. With insulin treatment, the diabetic mice can survive for several weeks, but the mortality rate in spite of insulin treatment is still approximately 50% at two weeks and uniformly lethal at four weeks.

NOD breeding colonies are commonly maintained by paired matings initiated at 4 to 6 weeks of age and continued until the animals are 20 to 22 weeks of age. This corresponds to the period of maximum breeding potential prior to the usual onset of lethal diabetes. Surviving animals usually are killed after breeding. Pozzilli et al., *Immunol. Today*, 14:193–96 (1993).

In order to obtain NOD mice that exhibit the symptomology of human rheumatoid arthritis (NOD-RA mice), mating of at least one nondiabetic NOD parent to produce possibly arthritic progeny is necessary. No incidence of RA symptoms developing in nondiabetic NOD parents has been observed.

When selecting parents (i.e., the parental generation, or $P_1$) for the method of the invention, at least one of the parents must be nondiabetic, that is, an NOD mouse that, although bred for the development of diabetes, fails to develop autoimmune diabetes. Preferably at least the female NOD mouse selected as a parent will be nondiabetic, more preferably both parents will be nondiabetic. Nondiabetic NOD parents should be diabetes-free, or euglycemic, and onset of diabetes in mice is signaled by marked hyperglycemia, i.e., rising and remaining above 250 mg/deciliter. Since the onset of diabetes is quickly fatal in NOD mice, the nondiabetic NOD animals useful for the purposes of the present invention are aptly referred to as survivors. In order to be sure that NOD mice selected for the purposes of the present invention are nondiabetic mice that will not develop diabetes, it is preferable that the parental mice selected be at least 12 weeks of age. Preferably the parental mice selected will be 20 weeks old or older, more preferably 22 weeks old or older, most preferably at least 24 weeks old. It is preferred also that the male and female parents selected for use according to this invention are age-matched, but this is not critical.

Nondiabetic NOD $P_1$ parents and $F_1$ offspring are truly nondiabetic, that is, they are not slow-onset diabetic mice that are destined to develop the disease later but fail to exhibit onset by the typical onset age of 20–30 weeks. None of the diabetes-free $P_1$ parents or $F_1$ progeny studied in the examples that follow died or developed detectable glucosuria during an additional ten months of observation. Furthermore, histological examination of their pancreases revealed no occult disease, i.e., no lymphocytic infiltration. Thus, the NOD-RA mice of the invention, as well as their NOD survivor parents are not diabetic mice useful for the study of autoimmune diabetes, and the present invention advantageously provides and alternative for nondiabetic survivors to destruction.

Although maintaining the NOD parents past the normal age of diabetes onset is a preferred way of isolating survivor nondiabetic NOD mice, it is not necessary to wait 20–30 weeks before practicing the present invention. Prediabetic screening of the mice is helpful in identifying nondiabetic NOD mice useful as parents in the practice of the present invention. Screening for glucose levels exceeding 250 mg/dl has been mentioned above, and additional pre-onset diabetic indicators include the appearance of autoantibodies against islets or insulin, the appearance of rheumatoid factor (RF), and increasing IL-6 levels. Although it is not usually practical to assay in mice, lymphocytic infiltration of the pancreas is also an indicator of diabetes onset, and therefore indications that the pancreas of an NOD mouse remains free of infiltrating lymphocytes also identifies a suitable $P_1$ parent for the purposes of the invention. Finally, since the nondiabetic NOD mice are, as mentioned above, born nondiabetic and will remain free of diabetes, mating of NOD mice without pre-determining whether or not they are nondiabetic may be done, with the development of NOD-RA offspring confirming after the fact that at least one of the parent mice was nondiabetic.

The $P_1$ matings of nondiabetic NOD pairs consistently produces $F_1$ mice that show high penetrance of RA symptomology by 20–28 weeks of age. Appearance of characteristic RA symptoms occurs. much sooner in $F_1$ females that become pregnant (e.g., 10–16 weeks after pregnancy).

The $F_1$ mice exhibit visible bilateral swelling of the ankles and the metatarsophlangeal and proximal interphalangeal joints of both hind feet. No swelling is typically observed at the distal interphalangeal joints. This pattern of joint swelling mimics the pattern characteristic of human RA.

The NOD-RA mice not only model the symptoms of human RA in overt physical characteristics, but also exhibit RA abnormalities upon clinical (e.g., radiological, histological, and serological) examination that closely resemble the symptoms observed in human RA patients. In addition, the penetrance of the RA-like disease in NOD mice is incomplete, as it is in humans, with identical twins of RA sufferers having less than 25% incidence lifelong of also developing RA. Also, there is a marked predominance (85%) of females in a population of $F_1$ mice that develop the RA disease, which is comparable to the predominance (75% females) found in human RA patients.

Not all $F_1$ mice will be NOD-RA mice (see Examples, infra.), and NOD-RA mice will usually begin to exhibit RA symptoms such as ankle swelling by 12 weeks of age, with peak onset at about 22–28 weeks of age.

The NOD-RA mice according to the invention may be used in any application where a mammalian model of human RA would be advantageous. The NOD-RA mice prepared according to the invention will be especially useful in testing RA diagnostic reagents, such as antibodies, dyes or magnetic resonance imaging agents, or in screening potential therapeutic agents. Many applications for such NOD-RA mice will immediately suggest themselves to persons skilled in this field.

A particularly useful application for the mouse RA model of the invention will be in drug screening. A method of screening utilizing NOD-RA mice according to the invention will comprise the step of administering to a NOD-RA mouse showing physical characteristics corresponding to human RA a candidate drug for the treatment of RA and then analyzing the mouse for improvement in any of the symptoms of the disease, e.g., lowering of RA or IL-6 levels, remission or decrease in, e.g., joint swelling, abnormal joint flexion or hyperextension, etc. Favorable change in the RA symptomology in the NOD-RA mice receiving the candidate drug will indicate that the candidate drug is useful for treating RA.

Another particularly useful application of the mouse RA model of the invention will be in screening for preventive medicines. Since the RA-like disease in NOD-RA mice has the same penetrance and gender and age dependence as in human RA patients, a good method for testing candidate RA preventive medicines will comprise administering a candidate medicine to the progeny of nondiabetic NOD mice, then observing whether the expected penetrance of the disease across all F1 progeny is altered in response to receiving the candidate medicine. If the incidence of appearance of RA across the F1 generation is reduced, if the severity of the disease is reduced, or if the onset of RA is delayed, then this indicates the that the medicine has preventive properties.

The NOD-RA mice according to the invention are further described in the examples that follow. These examples are illustrative of the methods and mice of the invention and are not intended to limit the concept of the invention in any way.

EXAMPLES

Ten surviving diabetes-free (euglycemic) NOD females at 24 weeks of age were mated with six age-matched diabetes-free NOD males. 175 $F_1$ offspring were categorized by monitoring for ankle swelling. Thirty-four of 87 female (39%) $F_1$ offspring and six of 88 male (7%) $F_1$ offspring of all ages exhibited ankle swelling. $F_1$ progeny exhibiting visible joint swelling were designated NOD-RA mice. Comparative colonies of BALB/c mice, parental $P_1$ NOD mice, and a cohort of ten new NOD females obtained from Jackson Laboratories were maintained as controls. None of the control groups exhibited periarticular swelling and appeared to have normal morphology of the peripheral limbs under similar aging and housing conditions.

Figure 1E:
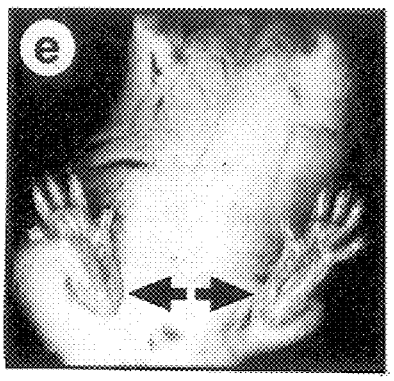
Figure 1F:
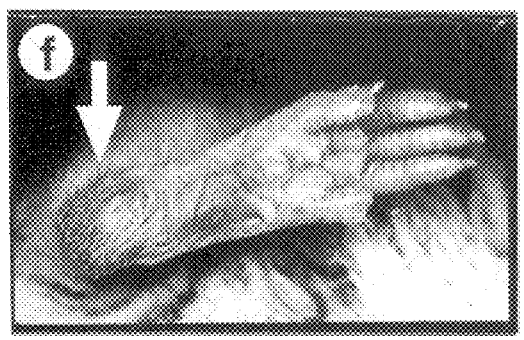

At 6 to 7 months (or 3 to 4 months following pregnancy), the NOD-RA mice showed grossly visible swelling of the ankles, as well as swelling at the metatarsophalangeal and proximal interphalangeal joints of both hind feet. No swelling was observed at the distal interphalangeal joints. Typical results are illustrated in FIG. 1, where hind feet of a 25-week-old BALB/c female (FIGS. 1a, 1b) are compared with the hind feet of a 25-week-old NOD-RA female (FIGS. 1c, 1d), the latter exhibiting moderate symmetrical peripheral fusiform swelling. FIGS. 1e and 1f show the hind feet of the same NOD-RA female at age 33 weeks and 8 weeks after pregnancy and delivery. It can be seen that the peripheral limb swelling is more pronounced.

Figure 1G:
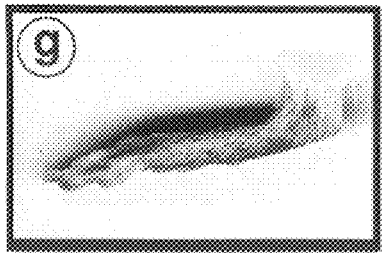
Figure 1H:
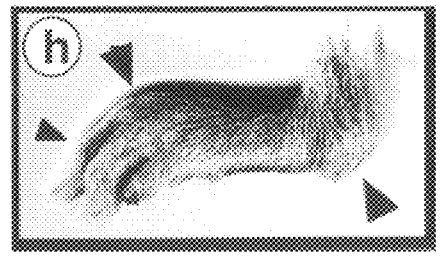

In FIGS. 1g and 1h, the hind feet of different 29-week-old BALB/c (FIG. 1g) and NOD-RA (FIG. 1h) mice are compared. Arrows indicate maximal swelling and joint abnormalities.

Figure 2A:
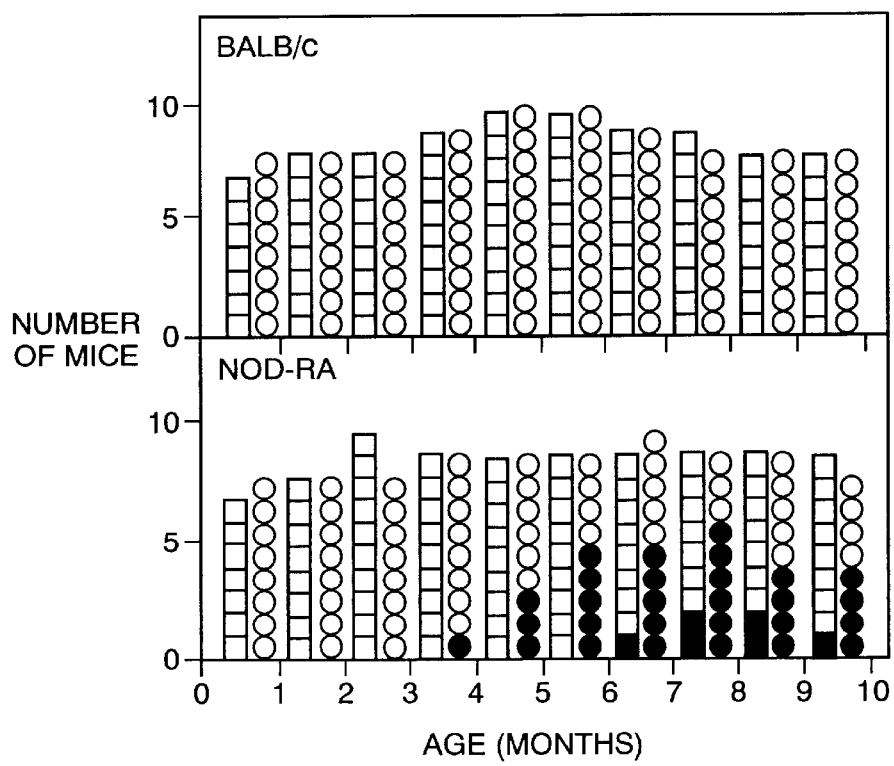
FIG. 2 (comprised of FIGS. 2*a* and 2*b*) illustrates age- and gender-dependent prevalence of RA in $F_1$ mice from non-diabetic NOD parents (FIG. 2*a*) and the effect of pregnancy on disease progression in female $F_1$ mice (FIG. 2*b*).
Figure 2B:
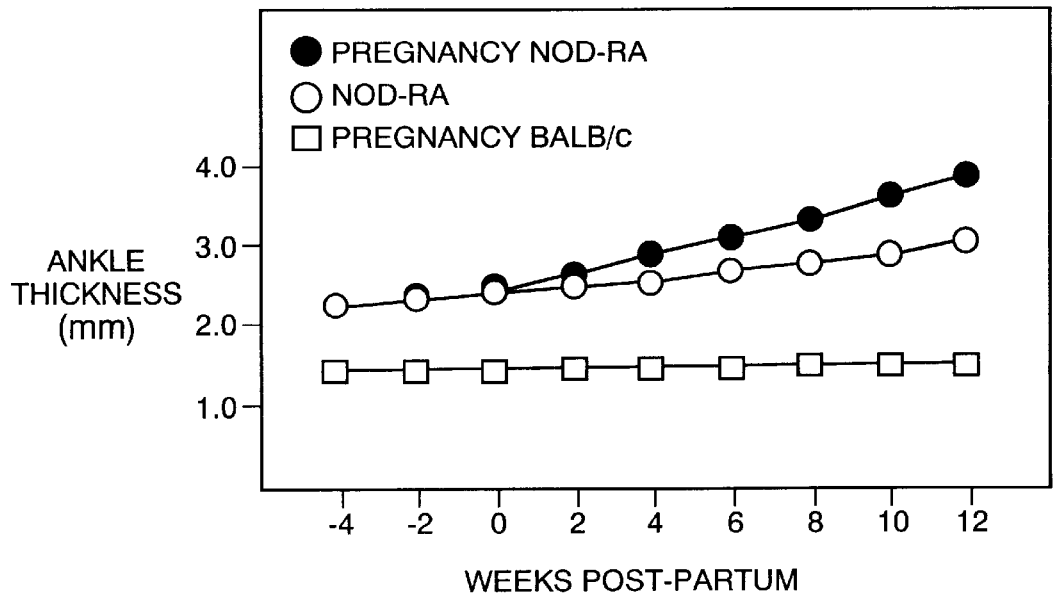

FIGS. 2a and 2b show statistical analysis of prevalence of RA in $F_1$ and the effect of pregnancy on disease progression, by compiling data on all $F_1$ progeny that were not sacrificed for histological analysis before 10 months of age.

FIG. 2a shows the prevalence of RA-like condition in $F_1$ mice of nondiabetic NOD parents. All mice were categorized by age and had ankle thickness measured using calipers. Those mice with an ankle thickness at least twice that of age-matched BALB/c controls are indicated by filled symbols (●, ■). Females are indicated with circles (○, ●) and males are indicated with squares (■, □).

FIG. 2b shows the effect of pregnancy on RA-like disease progression. Ankle thickness of $F_1$ female offspring of nondiabetic NOD parents was measured before and after pregnancy in $F_1$ NOD-RA females and in BALB/c females mated at 4 months of age. Ankle thickness in virgin $F_1$ NOD-RA females was also measured. The data shown in FIG. 2b are means of two animals in each group. A pronounced increase in ankle thickness is observed in NOD-RA females compared with the BALB/c female group, and additionally, a more rapid progression of RA is observed in the group of NOD-RA females that became pregnant. The remission of RA during pregnancy and exacerbation postpartum closely mimics a phenomenon long recognized in human female RA patients.

Figures 3A, 3B, 3C, 3D:
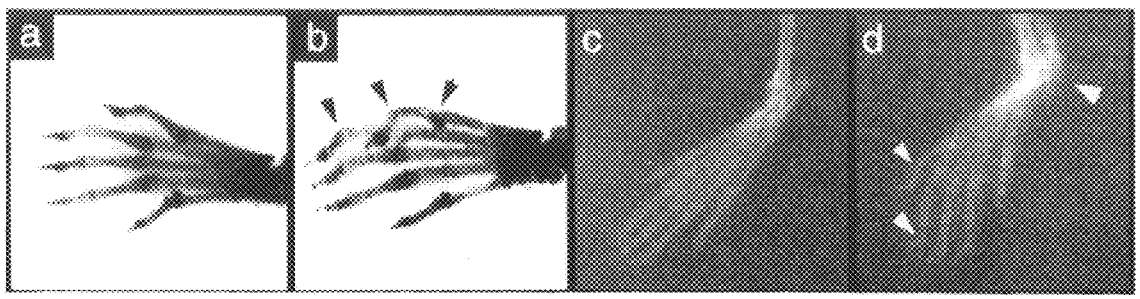
FIG. 3 (comprised of FIGS. 3*a* through 3*l*) illustrates histological and skeletal abnormalities in NOD-RA mice.

Skeletal examinations were made of NOD-RA mice and BALB/c controls at 7 months of age or older to characterize joint disease occurring in the former (see FIG. 3). Hind feet skeletons of BALB/c (FIG. 3a) and NOD-RA (FIG. 3b) mice were stained with Alizarin red and Alcian blue. Comparison of the NOD-RA (FIG. 3b) and BALB/c (FIG. 3a) skeletal specimens shows enlargement of the peripheral synovial joints and severe joint destruction in the NOD-RA animals. Arrowheads (FIG. 3b) indicate tendon rupture secondary to joint subluxation.

In FIGS. 3c and 3d, radiological analysis of the hind feet of BALB/c (FIG. 3c) and NOD-RA (FIG. 3d) mice shows obliteration of the ankle joint space, central osseous erosion of the ankle, and fusiform swelling of soft tissue extending from the ankle down to the digits of the NOD-RA animal. Arrowheads (FIG. 3d) indicate the locations of the radiographic deformities. Radiological and skeletal findings demonstrated that, in contrast to the peripheral joints, the sacroiliac and vertebral joints in NOD-RA mice were not affected.

Figures 3E, 3F, 3G, 3H:
Figures 3I, 3J, 3K, 3L:
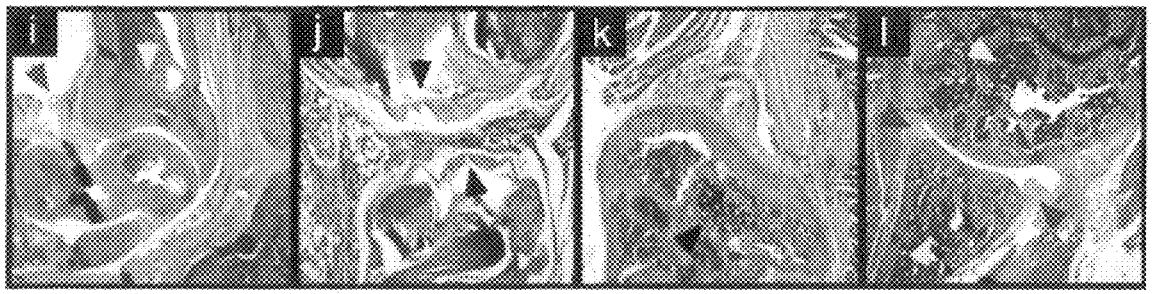

Histological micrographs (magnification 260×) were prepared of ankle, elbow, knee and metatarsophalangeal joints by staining with hematoxylin and eosin and are presented in FIGS. 3e to 3l. FIGS. 3e, 3f, 3g and 3h were prepared from a BALB/c mouse, and FIGS. 3i, 3j, 3k and 3l were prepared from an NOD-RA mouse. Ankle preparations are shown in FIGS. 3e and 3i; elbow in FIGS. 3f and 3j; knee in FIGS. 3g and 3k; metatarsophalangeal joints in FIGS. 3h and 3l. The joint histology of the NOD-RA animals is characterized by pannus proliferation and invasion of the articular space (light arrowhead, FIG. 3i), degradation of articular cartilage (dark arrowheads, FIGS. 3i and 3j), osseous erosion, and infiltration of inflammatory cells at the ends of the bones (FIGS. 3i and 3l). A multinucleated giant cell associated with bone and cartilage detritus is also apparent (FIG. 3l).

From radiological and histological evidence, it was seen that the disease was more prominent in the hind limbs than in the fore limbs and exhibited a distal-to-proximal gradient of severity, with general sparing of the distal interphalangeal joints of the limbs. The disease was bilaterally symmetrical in each mouse that developed the RA-like condition. In addition, examination of the spine and hips showed that the disease appeared to spare the axial skeleton, another phenomenon parallelling human RA. Knee joints exhibited a hypertrophic, edematous synovial membrane extending over the femoral condyles and into the intercondylar notches. As in the hands and feet of humans with advanced rheumatoid arthritis, spontaneous rupture of the extensor tendons of the fore and hind feet of the NOD-RA mice was common. Joint malalignment and subluxation were also apparent in skeletal preparations of the NOD-RA mice.

Boutonniere deformity, a common type of tendon rupture and joint deformity in humans with RA, is characterized by hyperextension at the metacarpophalangeal joint and flexion at the proximal interphalangeal joint. NOD-RA mice exhibited virtually identical tendon deformities in their feet, with rupture of extensor tendons with hyperextension at the metatarsophalangeal joint and flexion of the proximal interphalangeal joint.

In human RA, pannus formation in the early stages is confined to the margins of the joints but extends toward the joint capsule as the disease progresses, crosses the synovium and destroys the underlying synovial cartilage. A similar progression is evident in the elbow joints of NOD-RA animals (see FIG. 3j). Marrow inflammation and replacement of subchondral bone were evident in the long bones of the ankle (e.g., FIG. 3i), in the knee joint (e.g., FIG. 3k), and in the metatarsophalangeal joint (e.g., FIG. 3l) of the hind limbs of NOD-RA mice.

Examination of the pancreas of NOD-RA mice showed normal, well-granulated islets, with no evidence of lymphocyte invasion or surrounding lymphocytes, confirming that the NOD-RA mice were diabetes-free.

In human rheumatoid arthritis, onset of the disease is also characterized by serological phenomena. See, e.g., Jackson, in *Clinical Laboratory Medicine*, Tilton, ed. (Mosby Year Book, St. Louis, 1992), pp. 485–504. For example, about 70%–90% of RA patients produce "rheumatoid factor" (RF), which comprises autoantibodies specific for the Fc region of immunoglobulin G. In addition, markedly increased concentrations of the proinflammatory cytokine IL-6 are observed in the synovial fluid and serum of RA patients. Diverse patterns of autoantibody production have also been observed in humans with various autoimmune diseases including RA, such as antibodies to double-stranded DNA (anti-dsDNA), although anti-dsDNA antibodies are usually a more sensitive marker in humans for lupus erythematosus than for RA. To compare the serological profile of RA patients and NOD-RA mice, sera were examined in male and female BALB/c mice (controls), NOD mice (controls), NOD-RA mice, NOD mice with insulin-dependent diabetes mellitus (NOD-IDDM), healthy human donors and RA patients for RF, IL-6 concentration, and anti-dsDNA (see FIG. 4).

Figure 4A:
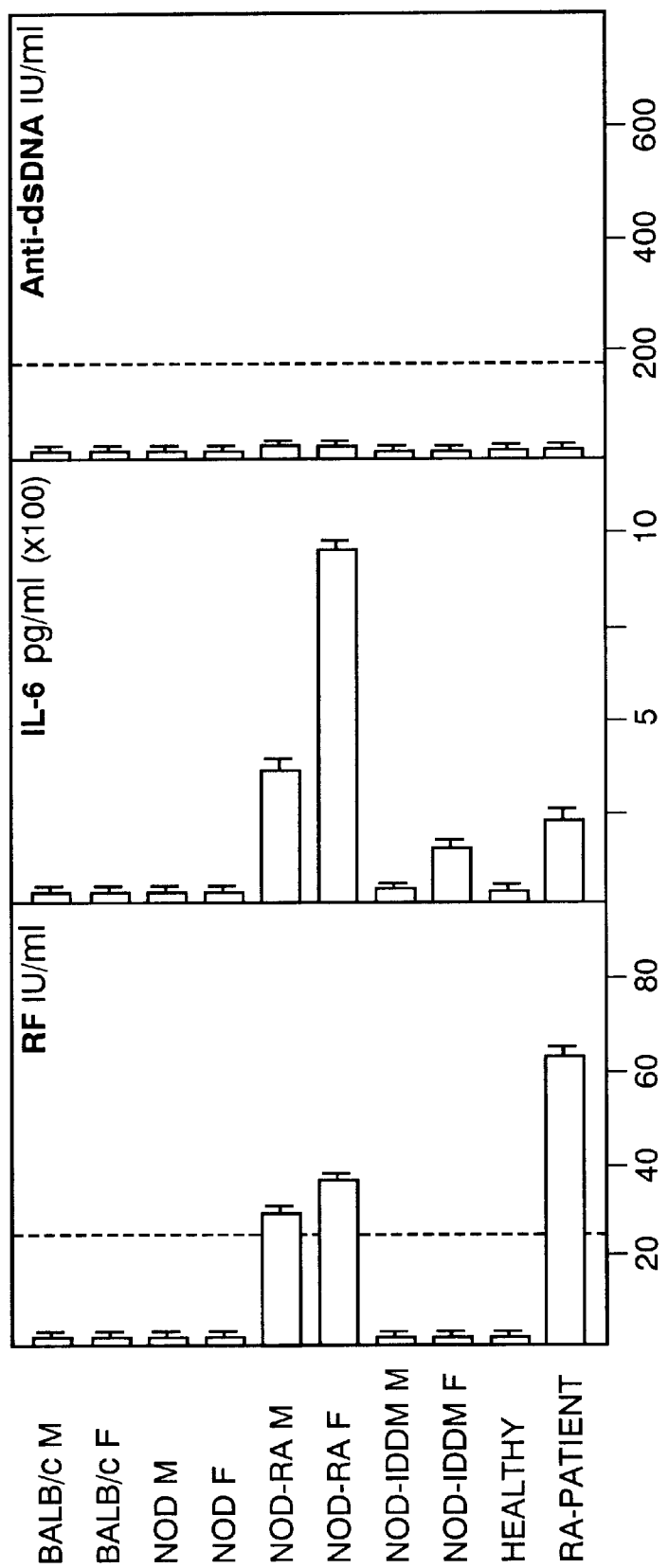
FIG. 4 (comprised of FIG. 4*a* and FIGS. 4*b* through 4*i*) shows serological comparisons between arthritic NOD-RA mice and non-RA mice (BALB/c male (M) and female (F), NOD M, NOD F, NOD-IDDM M, NOD-IDDM F) and between RA and non-RA humans (RA-Patient and Healthy, respectively). Levels of autoantibodies specific for the Fc region of IgG (RF), expression levels of inflammatory cytokine IL-6, and serum levels of anti-double stranded DNA IgG antibodies (Anti-dsDNA) are shown in FIG. 4*a*. Ankle joint synovial membrane samples of BALBc mice (FIGS. 4*b*–4*e*) and of NOD-RA mice (FIGS. 4*f*–4*i*), stained with hematoxylin and eosin (FIGS. 4*b*, 4*f*), antibodies to IL-6R$\alpha$ (FIGS. 4*c*, 4*g*), antibodies to IL-6R$\beta$ (FIGS. 4*d*, 4*h*), or normal rabbit IgG (negative control) (FIGS. 4*e*, 4*i*) are shown in FIGS. 4*b*–4*i*.

In FIG. 4a, concentrations of RF in IU/ml, concentration of IL-6 in picograms/ml, and levels of anti-dsDNA antibodies in IU/ml are shown for each group of subjects. The data presented are means +s.e. of values from three subjects. Abnormally high concentrations for RF (>25 IU/ml) and anti-dsDNA (>180 IU/ml) are indicated on the graphs by dotted lines.

Of the subjects examined, only NOD-RA animals (both male and female) produced RF at levels approaching that apparent in human RA patients. Similarly, both male and female NOD-RA mice, but none of the other subjects examined (except RA patients), exhibited high serum concentrations of IL-6. Antibodies to double-stranded DNA were not detected in the serum of any of the subjects examined.

Figures 4B, 4C, 4D, 4E:
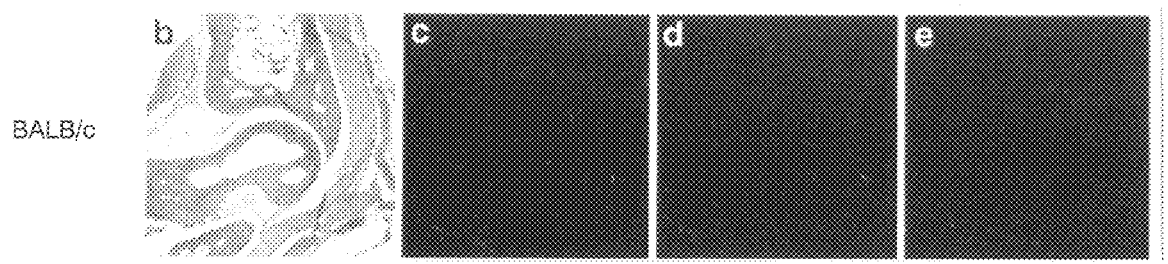
Figures 4F, 4G, 4H, 4I:
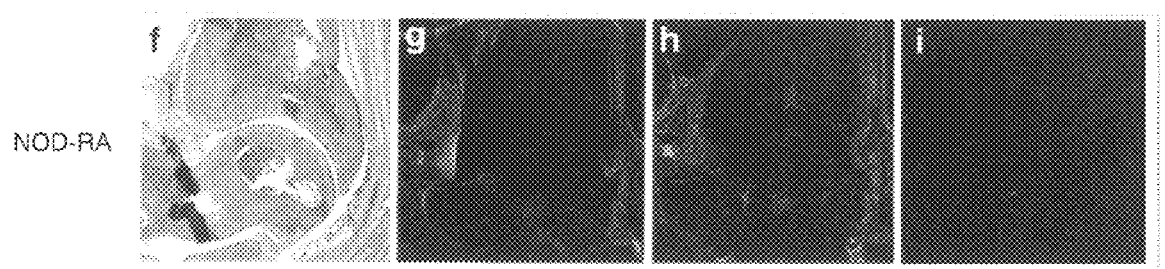

IL-6 receptor upregulated expression was also examined in histological specimens of ankle joints in BALB/c mice (FIGS. 4b–4e) and NOD-RA mice (FIGS. 4f–4i). Ankle joints of 30-week-old female mice were sectioned and stained with hematoxylin and eosin (FIGS. 4b and 4f), or stained using antibodies to IL-6 receptor α chain (IL-6Rα, FIGS. 4c and 4g) or antibodies to IL-6 receptor β chain (IL-6Rβ, FIGS. 4d and 4h). As a control, sections also were stained with normal rabbit IgG (FIGS. 4e, 4i). As can be seen from these histograms, marked expression of both IL-6 receptor subunits was evident in the abnormal synovial membrane of NOD-RA mice, in contrast to the BALB/c normal synovial membrane (FIGS. 4c, 4d), where only a few cells express the receptor.

From the foregoing discussion and data, it can be seen that the NOD-RA mice described herein provide a novel spontaneous model that closely mimics human rheumatoid arthritis. The NOD-RA model exhibits clinical, (e.g., radiological, histological and serological) symptoms that are typical of humans afflicted with rheumatoid arthritis. Also as with rheumatoid arthritis in humans, the disease in NOD-RA mice is spontaneous and dominant in females, with onset at older ages, incomplete penetrance in a population, lifelong exacerbation after pregnancy. The NOD-RA mouse model may consequently be used advantageously for characterization of the pathogenesis of RA in humans and may be used advantageously in the development and testing of new drugs and diagnostic reagents for treating and detecting or monitoring this prevalent human affliction.

The publications cited above are all incorporated herein by reference.

Variations and additional embodiments of the invention described herein will be apparent to those skilled in the art without departing from the scope of the invention as defined in the claims to follow. For instance, although the discoveries related herein pertain to the well-known NOD mouse, other strains of mice that develop autoimmune disease phenotypes, such as SJL mice, NZB mice, and NZW mice, which are prone to develop a lupus erythematosis-like disease, may also show in certain progeny the development of the rheumatoid arthritis-like disease found in the nondiabetic NOD progeny described above. Also, in view of the phenomena described above, common shortcuts such as lymphocyte transfer from NOD-RA mice to naive young NOD mice or, e.g., irradiated mice of other species will be expected to recapitulate the RA seen in the NOD-RA donors. Likewise, other mammalian species commonly used in laboratory experiments, such a guinea pigs and rabbits, which species are susceptible to autoimmune disorders, may be studied and bred in accordance with the discoveries detailed above to determine whether another species useful as a model for human rheumatoid arthritis can be developed.

What is claimed is:

1. A mouse model of human rheumatoid arthritis prepared by the process of:
   (a) breeding a nondiabetic NOD male mouse and a nondiabetic NOD female mouse; and
   (b) selecting from the progeny produced from step (a), a mouse that exhibits symptoms of human rheumatoid arthritis.

2. The progeny of a nondiabetic NOD male mouse and a nondiabetic NOD female mouse, wherein said progeny exhibits clinical symptoms of human rheumatoid arthritis.

3. The progeny according to claim 2, wherein said symptoms of human rheumatoid arthritis are selected from the group consisting of: joint and limb swelling, symmetrical enlargement of peripheral joints with sparing of axial skeleton (e.g., hips, spine), spontaneous rupture of extensor tendons, Boutonniere deformity, synovitis, pannus formation, cartilage destruction, bone degeneration, autoantibodies specific for the Fc region of immunoglobulin G. and increases in IL-6 in serum.

4. The progeny according to claim 2, wherein said nondiabetic NOD mice are characterized as nondiabetic by a method selected from the group consisting of:
   (a) survival to 20–28 weeks of age;
   (b) survival to at least 20 weeks of age without development of hyperglycemia;
   (c) absence of leukocyte infiltration of the pancreas; and
   (d) production of offspring having symptoms of human rheumatoid arthritis.

5. A process for producing a mouse, which exhibits a symptom of rheumatoid arthritis, comprising the steps:
   (a) selecting from a population of NOD mice a pair of diabetes-free mice;

(b) breeding said mice selected in step (a); and (c) selecting from the progeny of step (b) a mouse, which exhibits symptoms of human rheumatoid arthritis, wherein said selected mouse is a NOD-RA mouse.

6. The process of claim 5, wherein the pair of diabetes-free mice are approximately the same age.

7. The process of claim 5, wherein the pair of diabetes-free mice are age-matched and are at least 6 weeks old.

8. The process of claim 5, wherein the pair of diabetes-free mice are age-matched and are at least 12 weeks old.

9. The process of claim 5, wherein the pair of diabetes-free mice are age-matched and are 20–24 weeks old.

10. A method for isolating an agent useful for prevention or treatment of rheumatoid arthritis comprising: administering an agent to one or more progeny of two nondiabetic NOD mice and observing, with respect to the progeny, penetrance of rheumatoid arthritis symptomology across all such progeny, onset of any rheumatoid arthritis symptomology, or the magnitude of rheumatoid arthritis symptoms exhibited in any of the progeny, wherein an agent associated with decreased penetrance, delayed onset, or reduced symptoms indicates usefulness of the agent for prevention or treatment of rheumatoid arthritis.

11. A process for obtaining a mouse, exhibiting symptoms of rheumatoid arthritis, comprising breeding two diabetes-free NOD mice and collecting the progeny thereof that exhibit symptoms of human rheumatoid arthritis.

12. The process according to claim 11, wherein at least one of said collected progeny exhibit one or more symptoms selected from the group consisting of: joint and limb swelling, symmetrical enlargement of peripheral joints with sparing of axial skeleton, spontaneous rupture of extensor tendons, Boutonniere deformity, synovitis, pannus formation, cartilage destruction, bone degeneration, autoantibodies specific for the Fc region of immunoglobulin G, and increases in IL-6 in serum.

13. The process according to claim 12, wherein said diabetes-free NOD mice are characterized as diabetes-free by a method selected from the group consisting of:

(a) survival to 20–28 weeks of age;

(b) survival to at least 20 weeks of age without development of hyperglycemia;

(c) absence of leukocyte infiltration of the pancreas; and (d) production of offspring having symptoms of human rheumatoid arthritis.

* * * * *